(12) United States Patent
Li

(10) Patent No.: US 7,276,914 B2
(45) Date of Patent: Oct. 2, 2007

(54) SYSTEM AND METHOD FOR GUIDED TDR/TDT COMPUTERIZED TOMOGRAPHY

(75) Inventor: Jian Li, Newark, CA (US)

(73) Assignee: University of Delaware, Newark, DE (US)

(*) Notice: Subject to any disclaimer, the term of this patent is extended or adjusted under 35 U.S.C. 154(b) by 0 days.

(21) Appl. No.: 11/307,287

(22) Filed: Jan. 31, 2006

(65) Prior Publication Data

US 2007/0176605 A1 Aug. 2, 2007

(51) Int. Cl.
*G01R 31/11* (2006.01)
*G01R 31/08* (2006.01)

(52) U.S. Cl. ............... 324/534; 324/527; 324/555

(58) Field of Classification Search ......... 324/534, 324/512, 500, 718, 456, 216, 237, 238, 240, 324/637, 642, 533, 95, 527, 528, 555; 385/39
See application file for complete search history.

(56) References Cited

U.S. PATENT DOCUMENTS

| | | | | |
|---|---|---|---|---|
| 4,331,919 A | * | 5/1982 | Beckley | 324/222 |
| 4,706,021 A | * | 11/1987 | Chamuel | 324/242 |
| 5,006,788 A | * | 4/1991 | Goulette et al. | 324/95 |
| 5,144,151 A | * | 9/1992 | Thorne et al. | 250/559.42 |
| 5,539,657 A | * | 7/1996 | Utsumi et al. | 725/75 |
| 5,608,328 A | * | 3/1997 | Sanderson | 324/529 |
| RE35,561 E | * | 7/1997 | Mashikian et al. | 324/520 |
| 6,222,373 B1 | * | 4/2001 | Morrison | 324/534 |
| 6,532,215 B1 | * | 3/2003 | Muntz | 370/242 |
| 6,541,985 B2 | * | 4/2003 | Yankielun | 324/644 |
| 6,777,949 B2 | * | 8/2004 | Tsuji et al. | 324/501 |
| 6,784,662 B2 | * | 8/2004 | Schlicker et al. | 324/242 |
| 7,075,315 B2 | * | 7/2006 | Tanaka | 324/642 |
| 7,123,031 B2 | * | 10/2006 | Twerdochlib | 324/693 |
| 2005/0238037 A1 | * | 10/2005 | Dodds et al. | 370/420 |

OTHER PUBLICATIONS

Kak et al. *Principles of Computerized Tomographic Imaging*. "Ch 3: Algorithims for Reconstruction with Non-diffracting sources." IEEE Press, 1988.
Li et al. "Void Detection in Post-Tensioning Ducts Using Time Domain Reflectometry." 6th International Bridge Conference (IBEC), Boston, MA, Jul. 17-20, 2005.
Chajes et al. "Void Detection in Grouted Posttensioned Bridges Using Time Domain Reflectometry." Proc. of Transportation Research Board 82nd Annual Meeting, Washington, DC, 2003.
Chajes et al. "Nondestructive Evaluation to Pre- and Post-tensioned Tendons: Void Detection and Corrosion Monitoring." Presentation to International Bridge Conference, Pittsburgh, Pennyslvania, 2002.

* cited by examiner

*Primary Examiner*—Anjan Deb
*Assistant Examiner*—Hoai-an D. Nguyen
(74) *Attorney, Agent, or Firm*—RatnerPrestia

(57) ABSTRACT

A system for detecting a defect or discontinuity in media or at an interface of the media includes a signal generator; a transmission path coupled to the signal generator, wherein the transmission path is arranged along or through the media; a detection circuit for detecting a transmitted and a detected portion of a signal provided by the signal generator; and a circuit for analyzing the reflected portion and identifying a location of a discontinuity or defect in the media. A related method of detecting a defect or discontinuity in media or at an interface between the media includes establishing an electromagnetic energy path along or through the media; coupling electromagnetic energy into the path; detecting a reflected portion of the electromagnetic energy; and analyzing the detected portion so as to determine a position of the defect or discontinuity.

23 Claims, 13 Drawing Sheets

SYSTEM AND METHOD FOR GUIDED TDR/TDT COMPUTERIZED TOMOGRAPHY

BACKGROUND

This disclosure relates to detecting defects or discontinuities and their position in media or at the interface of multi-media.

Traditional computerized tomography, also known as computed tomography or "CT", is a term used herein to refer to a type of approach (not limited to computed or computer based, etc.) using "open" or free-space transmission of ultrasound or x-ray beams in a relatively confined area is known, and is used to great effect in the medical arts, for example. Traditional CT technology usually employs large number of projections from different angles to enhance resolution and show detailed structure of the object under investigation. Its objects, on the other hand, are usually very complicated such as human body, which also demand high resolution.

Further, Time Domain Reflectometry/Time Domain Transmission (TDR/TDT) is a known technique often used for determining the continuity or discontinuity of a transmission line, e.g., an antenna line or other transmission cable used in various electrical applications.

However, these individually powerful techniques are not known by the present inventor in combination in a way that would allow their use in detecting discontinuities and defects in various media on a relatively large scale, i.e., on a scale much greater than that which would be allowed in a confined clinical setting. Such large scale applications include, for example, a dam, building foundation, or a pipeline, to name just a few.

SUMMARY

Instead of open beam projection in traditional CT, one aspect of this disclosure utilizes electromagnetic fields (including light) that are bounded with wires, wave guides, optical fibers, etc. or other boundaries which can guide the electromagnetic fields or light through media along the projection path. This projection path is not one that an open beam naturally follows in traditional CT when traveling according to radiation, propagation, reflection, or other free-space transmission rules.

The projection paths of various embodiments of this disclosure may comprise man-made materials (e.g., transmission lines or optical fibers) that are capable of guiding the electromagnetic fields (including light) to propagate through media. The traditional technique of Time Domain Reflectometry/Time Domain Transmission (TDR/TDT) may be utilized to implement the electromagnetic field (or light) travel time analysis. Aspects of this disclosure provide an inexpensive, large scale, and flexible (plane or curvy interface) two-dimensional (2-D) or three-dimensional (3-D) discontinuity detection and locating system and method. It is worth noting that 2-D discontinuity detection is not typical in traditional CT.

In one embodiment, a method of detecting a defect or discontinuity in media or at an interface between the media which includes establishing an electromagnetic energy path along or through the media; coupling electromagnetic energy into the path; detecting a reflected portion of the electromagnetic energy; and analyzing the detected portion so as to determine a position of the defect or discontinuity.

In another embodiment, a system for detecting a defect or discontinuity in media or at an interface of the media includes a signal generator; a transmission path coupled to the signal generator, wherein the transmission path is arranged along or through the media; a detection circuit for detecting a transmitted and a detected portion of a signal provided by the signal generator; and a circuit for analyzing the reflected portion and identifying a location of a discontinuity or defect in the media.

In yet another related embodiment, a grid network sheet includes a plurality of transmission paths arranged in a grid, wherein a portion of the plurality of transmission paths overlap another portion of the plurality of transmission paths, and wherein each of the plurality of transmission paths is electrically disconnected from any every other one of the plurality of transmission paths.

To summarize the novel features of this disclosed approach, TDR/TDT CT or Guided TDR/TDT CT can be applied where it needs continuous or occasional monitoring. Such an application is relatively inexpensive, simple, and repeatable, and provides a heretofore unknown ability to conduct large-scale applications where traditional CT is either inconvenient, impractical, or impossible to implement.

The system and method of the present disclosure uses man-made materials to form a guided path for electromagnetic fields (or light) to project the energy in media rather than a naturally formed path for open beam in traditional CT. This kind of guiding path is very easy to build, and can be of many forms as long as it guides electromagnetic fields or light and has the necessary ability to interact with the local environment. Examples of guiding paths compositions include TV twin leads, ribbon cables, wires, conductive plates, optical fibers and many other types.

The system and method of the present disclosure uses guided electromagnetic fields (or light) propagation rather than other open beams such as X-ray, ultrasound, Magnetic Resonance (in MRI, Magnetic Resonance Imaging).

Because the path is composed of man-made guide, the path can be manipulated in a straight or a curved form, and thus can be used to detect discontinuities on plane or curvy interfaces, and to utilize the symmetric or other geometric features of the object under investigation to lower the complexity of monitoring and analysis. This is different from other CT applications where open beams can only travel in straight or quasi-straight paths or other paths that are formed by physical rules rather than human manipulations.

The system and method of the present disclosure uses a time-line integral as a theoretical basis where the time integral for the guided path is measured or calculated. In contrast, traditional CT applications involve the application of more complex attenuation integral or other forms of integral. TDR/TDT is the tool to measure and calculate time elapse that is a novel application.

BRIEF DESCRIPTION OF THE DRAWINGS

A better understanding of the inventive concept may be obtained from the various drawing figures in which.

DETAILED DESCRIPTION

Figure 1:
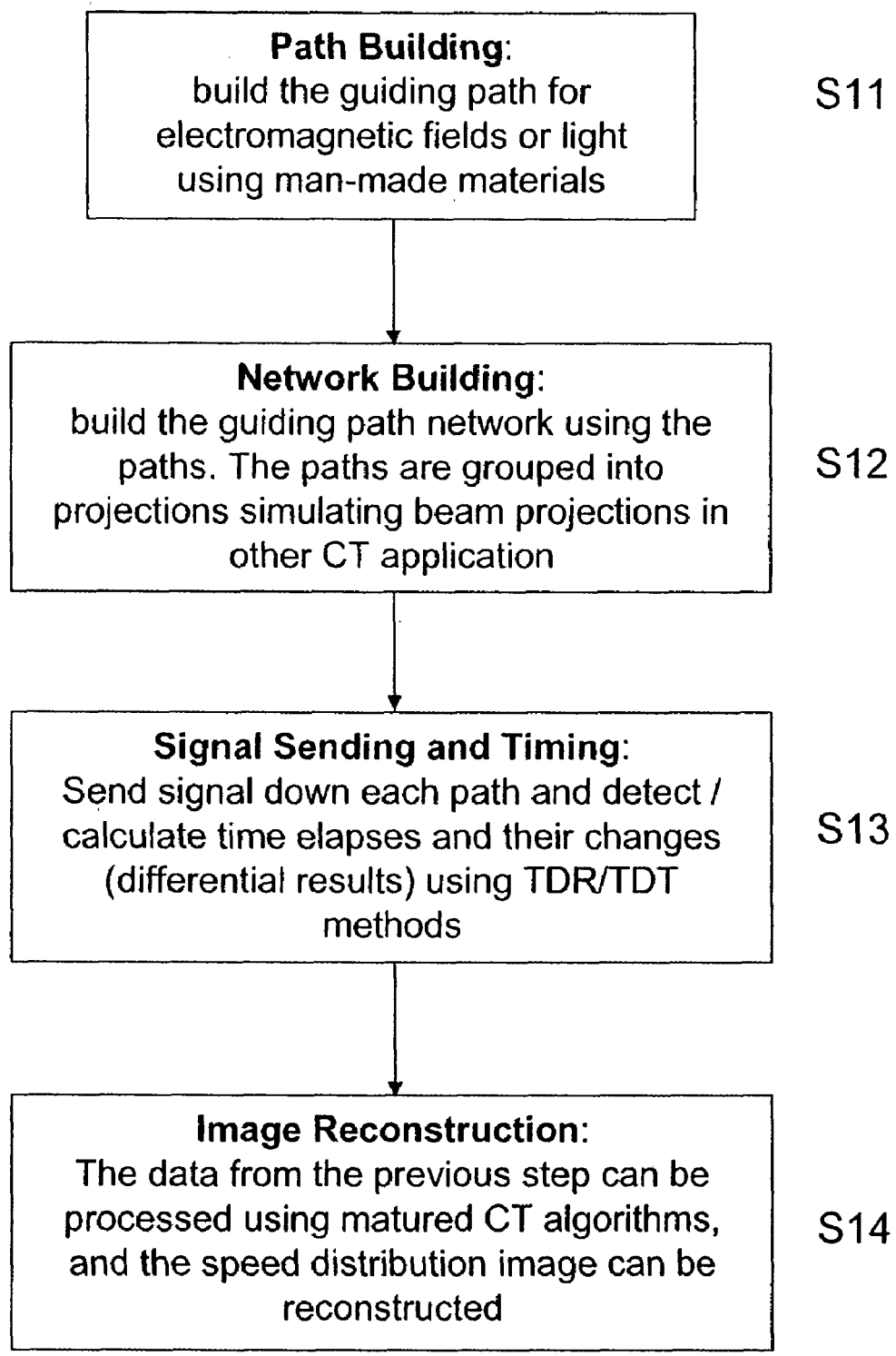
FIG. 1 notionally depicts the steps in a method for dealing with a planar media interface.

Various embodiments of the TDR/TDT CT (or Guided TDR/TDT CT) system and method of this disclosure will now be discussed in detail with reference to the drawings, where appropriate.

When electromagnetic fields (or light) travel along a man-made guided path, e.g., a transmission line or optical fiber, it generally is controlled by the following equations:

$$X_0 = \int_0^{l_0} 1/speed(x, y, z) dl \tag{1}$$

$$X = \int_0^{l_0} F(x, y, z) dl \tag{2}$$

In equation (1), $X_0$ indicates the total elapsed time for the EM energy travel which can be calculated and recorded using TDR/TDT technology. The travel along the path can be counted as either a signal reflection or transmission. The path section designated as "$I_0$" indicates the section of the path over which $X_0$ is calculated. The function speed (x, y, z) indicates the speed of propagation at the position (x, y, z) on the path $I_0$. Because speed (x, y, z) is defined by electromagnetic properties of the media together with some other factors such as the geometry of the guiding path at position I, thus, speed (x, y, z) may not be a constant and is vulnerable to the local electromagnetic properties at point (x, y, z). When local electromagnetic properties change due to time elapse or other reasons, speed (x, y, z) will also change and thus $X_0$ will change.

A differential $X(\Delta X = X - X_0)$ may be calculated by subtracting the current time integral result obtained from TDR/TDT technology from the original result, and equation (2) shows this change: Differential X represents the differential result for this path, and F(x, y, z) represents a property function which comprises the information of local electromagnetic (or optical) properties at position (x, y, z).

This equation fits into a general description equation of linear integral that is the theoretic basis of traditional CT applications:

$$P = \int_l f(x, y, z) dl \tag{3}$$

where P is a measured value or derived value from measured value, and f(x, y, z) is the distribution function of the parameters of a media. The line "l" is the line along which the integral is calculated. In traditional CT applications, this line is the path that the open beam travels according to free-space propagation rules, and thus frequently it is a straight line or quasi-straight line.

For example, in x-ray imaging where the x-ray intensity is attenuated by the material through which the x-ray energy is passing, i.e., the intensity $A = A_0 e^{-\delta x}$, where $\delta$ is a constant attenuation factor for the material along the pathway x. However, if $\delta$ is not constant throughout the material, then $$\ln \frac{A}{A_0} = \int_X \delta(x) dl \tag{4}$$

where A is an intensity at a particular point in the material, $A_0$ is the original intensity, $\delta$ is a variable attenuation factor that may depend upon the material and/or location in the material.

A transmission line which behaves according to a known distributed element model comprising distributed values for inductance (L) and capacitance (C) includes functions of permittivity (or dielectric constant) ($\epsilon$) and magnetic permeability ($\mu$), i.e., $L = f(\epsilon, \mu)$ and $C = g(\epsilon, \mu)$. Magnetic permeability is relatively constant for many materials, but permittivity is more variable across a variety of materials.

For a vacuum, the speed of light is $c_0 = 3.0 \times 10^9$ m/s, but in other materials, the speed of light is different than that in a vacuum. In this situation, the total elapsed time for the EM energy travel may be found by:

$$X = \int_l f(\mu, \epsilon, x) dl. \tag{5}$$

The present inventor observed that Equations (4) and (5) are similar in form, thereby establishing the theoretical basis for use of guided TDR CT as disclosed and claimed in the present disclosure, in a similar manner to the operating theory of X-ray CT. The left-hand side of these equations represent known measured or calculated values, and the right-hand side is a function of interest in integral form.

A group of linear integrals comprise a projection in CT, and many projections comprise the whole information package utilized by CT. After the data (Pin equation (2)) of these projections from different angles or directions are collected and processed, the function f(x, y, z) can be reconstructed mathematically.

Traditional X-ray CT utilizes many projections or free-space paths in order to provide the image resolution required for medical imaging applications. The more projections, the better resolution that may theoretically be obtained. The same general principle holds true in TDR CT, i.e., in a pulsed voltage implementation, discussed below, the more transmission line "projections", the better any reconstructed image and its resolution will be.

Because TDR CT shares a similar form as for a traditional CT for a single line integral, when similar groups of line integrals are composed and data (X in equation (2)) are collected and processed, the function F(x, y, z) can be reconstructed mathematically.

The time integral mentioned above may include, but is not limited to:

1. pulse edge shift (for example, step pulse reflection ending shift) due to the change of propagation speed accumulation (integration) over the length of the transmission line.

2. phase shift (for example, light or EM wave traveling from beginning to end of a transmission line will have a certain amount of phase difference accumulation over the length.

This phase difference could change over time, and can be detected by TDR/TDT techniques. Phase shift is similar to pulse edge shift in the sense that they are both incurred by speed difference accumulation. However pulse edge shift usually uses step pulse or pulses in other shapes which has an "edge" or "peak" characteristic to indicate the movement while phase shift uses "phase" which has to be interpreted more or less.

It is theoretically possible that another type of shift (e.g., accumulation or integration) that could be analyzed using time domain methods which may not be known at this time.

Thus the time integral could be pulse propagation speed integration (such as pulse edge shift), phase shift integration, etc.

Further, the EM pulse could be any as long as it can be analyzed using time domain characteristics and techniques. For example, a step pulse is good for edge shift analysis, and a single frequency EM pulse could be used for phase shift analysis. Other pulse types may also be useful as long as it can be interpreted by use of time integration related (e.g., phase shift is related to time).

One difference between Guided TDR/TDT CT and traditional CT is that a man-made guiding path is employed in Guided TDR/TDT CT. This path is a man-made one, i.e., not free-space propagation, and is used as a guiding path for electromagnetic field (or light) energy to propagate through media or a media interface and, at the same time, allows the energy to interact with media to get local electromagnetic (or optical) properties involved, i.e., a property that might be affected by the environment or media with which the energy interacts, for example, permittivity. The interaction can be detected and conditions in the media can be determined by the nature of the interaction.

This is quite different from traditional CT where only free-space "open" beams such as ultrasound, X-ray, etc. are employed. Once these beams are propagated from the source, they follow physical rules rather than being manipulated by a human in a "guided" way. Because a guiding path can be easily manipulated into straight or curvy shapes, Guided TDR/TDT CT opens a door to many novel application fields where traditional CT cannot be applied. One example is a curvy interface where Guided TDR/TDT CT can play a relatively easy role while traditional CT is incapable of providing meaningful results.

Another difference is the large scale range that Guided TDR/TDT CT allows. Electromagnetic fields (or light) can travel much further along a guided path while interacting with the surrounding environment or media and deriving information from the interaction. Traditional CT, on the other hand, relies mainly on the penetration ability of the open beams whose attenuation is significant along the path and thus hampers its effective range. In small-scale applications, TDR/TDT CT can also be applied. Thus Guided TDR/TDT CT has a much larger range of potential applications than does traditional CT.

Yet another difference is that Guided TDR/TDT CT use TDR/TDT technology to measure elapsed time and time integral data. This is rarely, if ever, the case in other traditional CT applications.

Major components in TDR/TDT CT include the man-made energy guiding path, CT analysis of acquired data, and the time integral analysis. The time integral can be of many forms as long as it is related to time (pulse edge propagation speed, phase propagation speed, etc., with no theoretical limit on what form it takes). The EM waves can take any form too, e.g., a step pulse, sinusoidal wave, or any form of periodic wave, as long as the practitioner can interpret it in a time-related fashion, e.g., edge shift, phase shift, or peak shift.

Particular embodiments of this disclosure will now be discussed with respect to the Drawings, where relevant.

In one embodiment, a method of detecting a defect or discontinuity in media or at an interface between the media, the method includes establishing an electromagnetic energy path along or through the media. The media could be the earth, concrete, an oil pipeline, aircraft, or any number of other articles or structures. Electromagnetic energy is coupled into the path, and then a reflected portion of the electromagnetic energy is detected. The detected portion may then be analyzed so as to determine a location or position of the defect or discontinuity along the transmission path.

Figure 4:
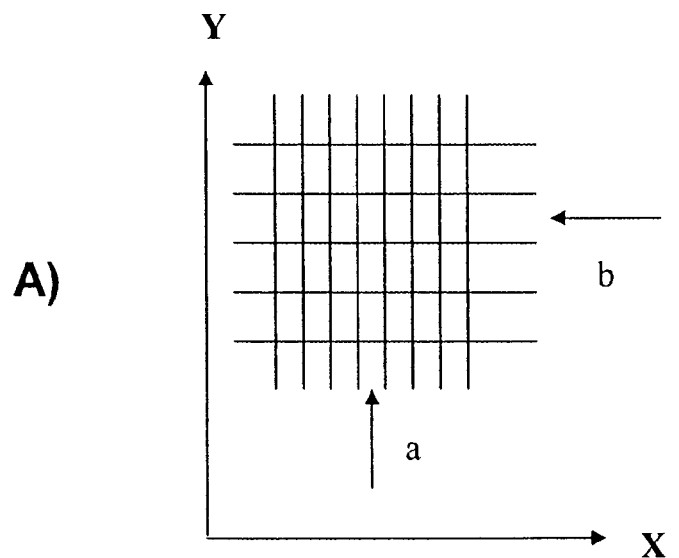
FIG. 4A illustrates a TDR CT network sheet in a rectangular grid form.
FIG. 4B illustrates a TDR CT network sheet in a triangular grid form.
FIG. 4C illustrates a TDR CT network sheet in another grid form.
FIG. 4D illustrates a TDR CT network sheet in a three-dimensional grid form.
Figure 4:
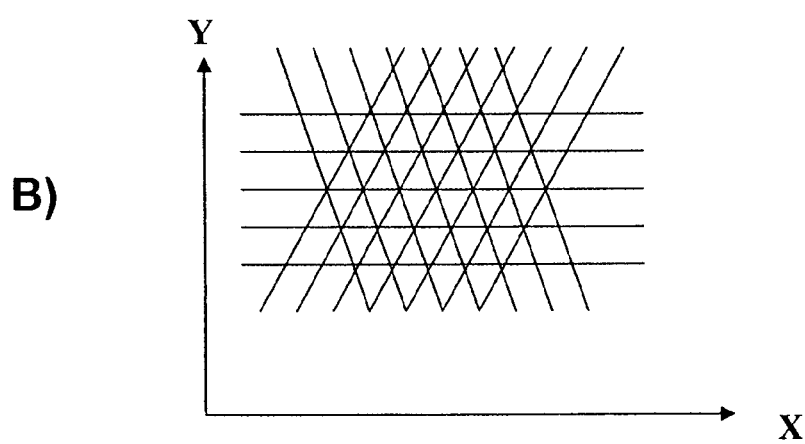
Figure 4:
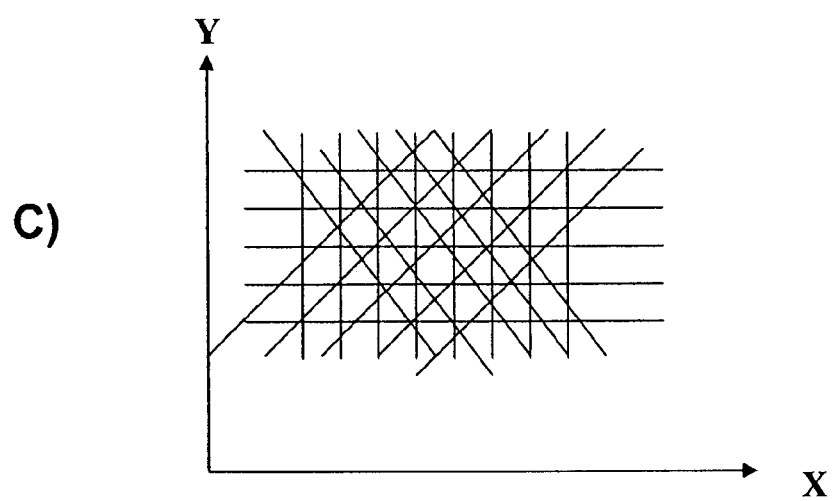

In another aspect of this embodiment, the electromagnetic energy path is established using a grid arranged along, through, or around the media or interface of interest. For example, the grid may be a two-dimensional (2-D) grid or a three-dimensional (3-D) grid. Three examples of 2-D grids are provided in FIGS. 4A-4C and an example of a 3-D grid is provided in FIG. 4D.

The energy coupled into the transmission path may be in the form of a step pulse voltage, and may further include analyzing the detected portion using a TDR/TDT technique.

In a further aspect, an image relating to the defect or discontinuity may be reconstructed using a known computerized tomography technique and displayed on a video monitor, for example, or it may be printed.

As mentioned above, the coupled electromagnetic energy may be in the form of either pulsed or RF energy. However, in an alternative implementation, the coupled electromagnetic energy may be in the form of light energy, e.g., laser light and appropriate optical fibers may be used for the transmission path.

To aid in analysis over time, the method may also include establishing a baseline condition of the media or interface at a first time value, and then determining a condition of the media at one or more times after the first time value. The different conditions may then be compared to the baseline condition to assess a change or deterioration of media or interface over time.

Figure 6A:
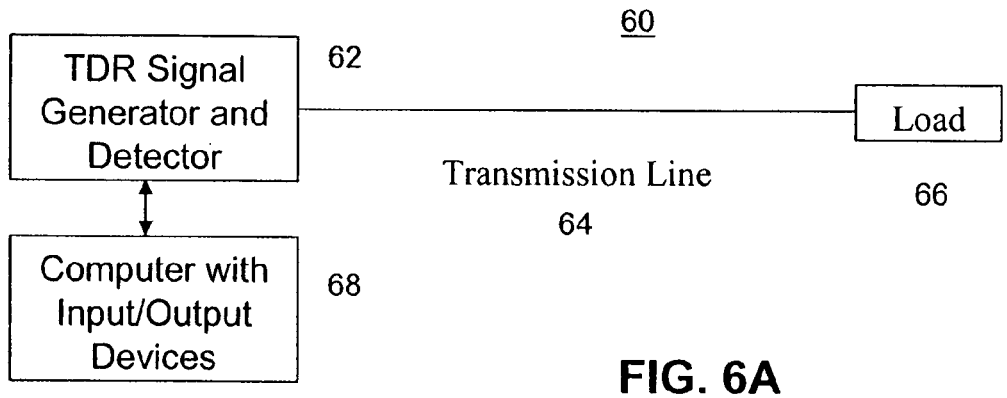
FIG. 6A provides a block diagram of an embodiment of a guided TDR CT system.

In another embodiment, illustrated in FIG. 6A, system 60 is capable of detecting a defect or discontinuity in media or at an interface of the media. System 60 includes a signal generator 62 and a transmission path 64 coupled to signal generator 62. Transmission path 64 may be arranged along or through the media (not shown) so as to have a transmission/reflection characteristic affected by the media or media interface. A detection circuit (part of signal generator 62) is arranged to detect a transmitted and a detected portion of the signal provided by signal generator 62. Load 66 may be a short-circuit load to ensure reflection of more energy to ease detection requirements. The detection circuit in 62 may include a detector or suitable electronic/computer circuit to analyze the reflected portion of the energy. From this analysis, e.g., time domain analysis of time delays, the position of a discontinuity or defect in the media may be localized.

In FIG. 6A shows a typical signal sending and detecting process on one transmission line in a TDR CT application. Load 66 is usually manipulated as an open-circuit end or short-circuit end to increase the reflections from the end, and thus make the tail movements (see FIGS. 6B and 7F) clearer in time. Loads at other impedances may be also applicable according to different application features.

Figure 6B:
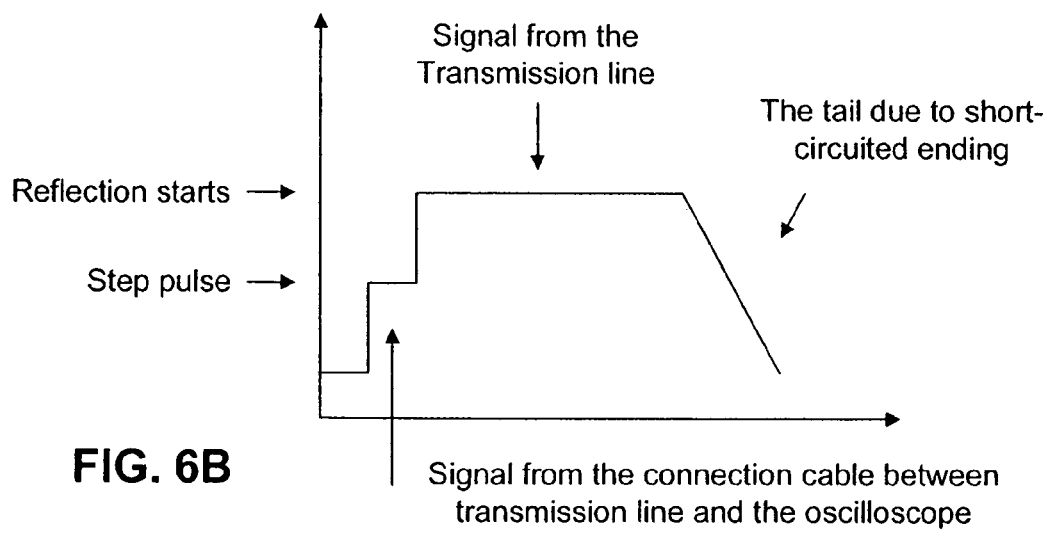
FIG. 6B illustrates a typical TDR plot showing timing data of a reflected pulse.
Figure 6C:
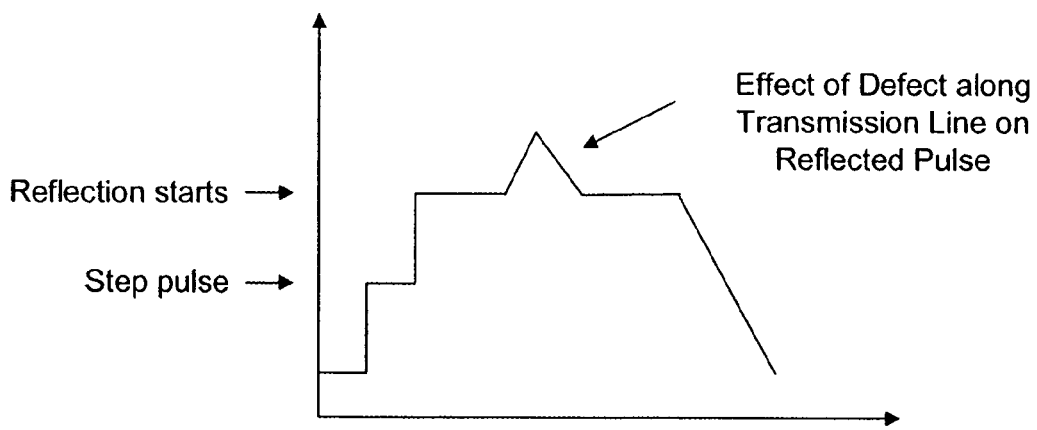
FIG. 6C illustrates a TDR plot showing the effects of a discontinuity or defect in the media along the transmission path.

FIGS. 6B and 6C depict a TDR plot for a continuous media and for a media with a defect, respectively. By known TDR calculations, the position of the defect may be localized.

Figure 4D:
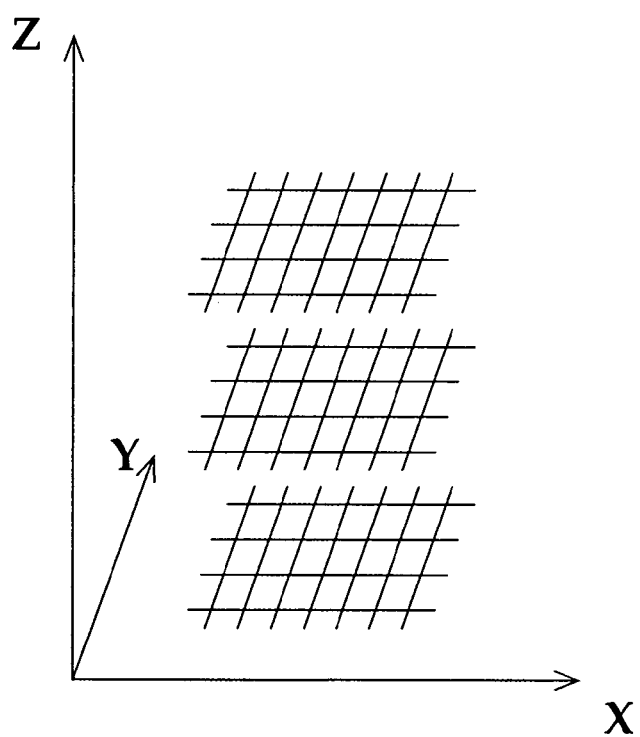

In another aspect of this embodiment, the transmission path includes a plurality of paths arranged in a grid along, through, or around the media. For example, the grid may be 2-D planar grids as depicted in FIGS. 4A-4C, or may be implemented as a 3-D grid as depicted in FIG. 4D.

In another aspect, the signal provided by signal generator 62 may be a pulsed signal, and the analysis circuit may include a TDR analyzer (shown for simplicity as part of 62).

In another aspect, computer or computer circuit 68 may be suitably programmed to construct or reconstruct an image representing the media or media interface, particularly at a point or points where a defect or discontinuity is located. Further, computer circuit 68 may reconstruct the image using a computerized tomography (CT) technique. Computer 68 may also include several peripheral and internal devices, e.g., memory, hard disk, network connectivity, printers, displays, etc.

System 60 may utilize a pulsed signal from signal generator 62 that appears as RF energy in the frequency domain, or a laser or laser diode may be used to generate light energy.

Computer or processor 68 may be suitably programmed to establish a baseline condition of the media at a first time value. Thereafter, a condition or conditions of the media may be determined at times after the baseline condition is recorded. The condition of the media after the baseline is determined may be compared to the baseline condition to identify a trend relating to the media and/or media interface.

Transmission path 64 may be a transmission line, e.g., a flat ribbon transmission line or other suitable transmission lines, and it may be short circuited (to aid in TDR analysis) at an end located away from signal generator 62. The end of the transmission line may be located at some distance away from generator 62, e.g., kilometers away. The shape of transmission line or path 64 can be of straight shape or of any curved shape. Alternatively, with an appropriate generator 62, e.g., laser or laser diode, the transmission path may be an optical fiber.

In another embodiment, a grid network sheet such as depicted in FIGS. 4A-4C is suitable for use with the system and method described above. In general, a grid network sheet includes multiple transmission paths arranged in a grid. A portion of the transmission paths overlap other transmission paths. The transmission paths have no direct electrical contacts or intersection points with each other.

In another aspect of this embodiment, the transmission paths are arranged in two or more groups of overlapping transmission paths. For example, the grid network sheet may include two groups of overlapping transmission paths arranged in a rectangular grid. FIG. 4A shows the TDR CT network sheet in rectangular grid form. Two groups of projection lines are employed here in perpendicular or quasi-perpendicular X and Y directions to form the grid. The two groups of projections can have their own spacing a and b. The choices of a and b can be decided by the resolution requirement and defect sizes that are necessary to be detected and/or resolved.

The grid network sheet may include three groups of overlapping transmission paths arranged in a triangular grid. The transmission paths may be separated by 120 degrees or some other desired angles. FIG. 4B shows the TDR CT network sheet in triangular grid form. The spacing within each group is flexible and can be equal or different. The choices of spacing can also be decided by the resolution requirement and defect size. The three groups of projection lines have no direct common intersection points.

The grid network sheet may include four groups of overlapping transmission paths arranged in a grid. The transmission paths may be separated by 90 degrees or some other angles. FIG. 4C shows the TDR CT network sheet in 90-degree (or other angles) grid form. The spacing within each group is flexible and can be the same or different. The choices of spacing can also be decided by the resolution requirement and defect sized. Furthermore, the number of groups of projections is not limited to 2, 3, or 4, and it could be as large as possible, such as 5, 6, and above, depending on resolution requirements and defect sizes to be detected and other practical considerations.

In an alternative embodiment, the grid network sheet may completely surround an object, e.g., a pipe such as an oil pipeline.

In another aspect of this embodiment, the transmission paths include a transmission line suitable for propagating a voltage pulse and, in another aspect, the transmission paths may include an optical fiber suitable for propagating a light pulse.

All these configurations of network sheets can be manipulated in plane shape or curvy shape and thus can be applied at both plane interface (or surface) and curvy interface (or surface).

EXAMPLES

Three general examples of Guided TDR/TDT CT applications are discussed below, i.e., planar format, curvilinear or "curvy" interface format, and a 3-D format. These 3 examples are used merely to illustrate the inventive concepts of this disclosure, and are not intended to restrict or impose a particular claim interpretation, and does not mean these examples are the only arrangements, solutions or methods of using Guided TDR CT.

Example 1

Planar Interface

Assume that we are facing the following problem: we have a media of concrete, and a media of water and their interface is a plane, and the dimension of the plane is relatively large compared to current CT technology. Assume also that water will gradually penetrate into the concrete in a very slow process. The question is, can we monitor the situation of penetration, such as when the penetration to a certain depth occurs, how much area has been penetrated, where are the areas, how these areas develop with time, etc.

If we analogize this interface to a cross sectional plane of a human body being scanned using X-ray from the side with image-reconstruction using traditional CT reconstruction method, then it is a very simple question. We just need to choose different angles for projections and then use X-ray to make these projections and use detectors to record the X-ray intensity attenuation. Thereafter, when the detector data are processed, the image of the intersection plane can be reconstructed and discontinuity areas can be identified.

However, in this real-world problem, concrete is not suitable for X-rays because: (1) Installing an X-ray CT system for concrete is not convenient or practical, and could be very expensive; it is obsolete to just install X-ray CT for one plane rather than for a multi layer; (2) This concrete type of application usually happens in dimensions of meters to even kilometers; X-ray, ultrasound or other traditional CT energy sources have no way to extend their range to this kind of real-world application in the field; and (3) X-ray will be greatly attenuated in concrete.

Lets now see how this problem could be solved using the present disclosure, i.e., using Guided TDR/TDT CT. In this solution, we are using electromagnetic fields. Our major steps notionally depicted in FIG. 1 include the following steps:

Step S11: Building the electromagnetic guiding path to simulate the X-ray beam in X-ray CT.

Step S12: Building the guiding path network to simulate the projections in traditional CT applications.

Step S13: Sending the electromagnetic pulses or signals down the guiding path and use TDR/TDT method to record the time elapse, and calculating differential results if needed.

Step S14: Collect the data on recordings and differentials and process to plot the function F(x, y, z) distribution chart to find out the water penetration area Path building: a two-wire transmission line can be used. This could be done very easily, i.e. a TV twin-lead cable can be a good example. Or we can use two very thin metal wires with a constant space between them and then use an insulation material to keep the conductors parallel to each other.

Guiding path network building: A projection will be build using many two-wire transmission lines in parallel, or in other forms including fan, cone, etc. Current CT techniques can handle different geometries of one projection. These techniques can also be applied here. Multi-Projections are then formed with several projections. The number of projections can be decided according to the nature of the problem and resolution required. All of these projections comprise the guiding path network.

Signal sending and timing: Electromagnetic step pulses, or peak pulses or other form of signals can be sent down through each guiding path (transmission line), and then time elapse can be measured or calculated using TDR/TDT technology.

Image reconstruction: Once all data are collected, the speed distribution plot can be drawn after image reconstruction. CT technology can provide sufficient help.

Example 2

Curvilinear ("curvy") Interface

Figure 2:
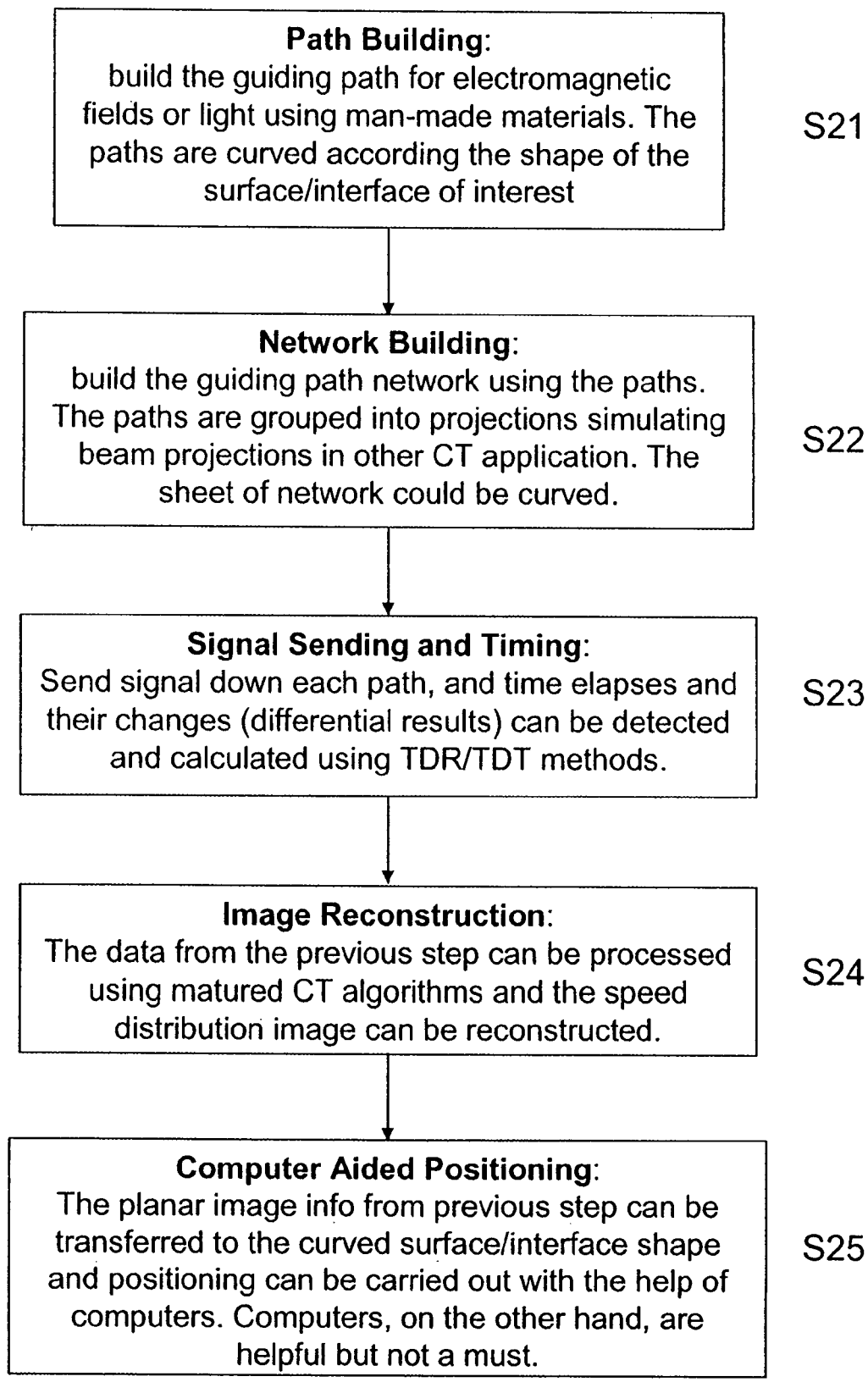
FIG. 2 notionally depicts the steps in a method for dealing with a curvilinear ("curvy") media interface.

FIG. 2 notionally depicts the following in steps S21, S22, S23, S24, and S25.

Lets assume we need to monitor the surface of an object that could be the surface of an oil pipeline, an airplane, an automobile, the Space Shuttle, or may be just a dam in a curvy or complex shape. X-ray or other open-beam CT technology cannot handle these types of problems.

A sheet of guiding path network can be buried beneath the surface which will follow the detailed shape of the surface and keep a constant distance from it. The shape and geometry information of the object can be stored in a computer.

Then we can easily find that this problem can actually be solved using the solution introduced in the planar example above because guided electromagnetic paths can guide the fields through curvy interfaces. The only difference is that the position of the defect or discontinuity cannot be directly distinguished by reading the TDR/TDT timing plot like in a planar situation. With the help of computer-processed information, however, this problem can be easily solved. The distance information obtained in TDR/TDT can be calculated and transferred into a curvy interface distance integral, and computers can easily fulfill this job and accurately indicate the position on the curvy interface.

This major change in the solution for a curvy interface from a plane is not complex considering that computer technology has advanced. It, however, greatly expands the usage of TDR CT to Guided TDR CT where any shape of interface is theoretically available for monitoring. This advantage stemming from man-made guiding path also eliminates the possibility of other traditional CT applications in this field.

Example 3

3-Dimensional (3-D) Application

Figure 3:
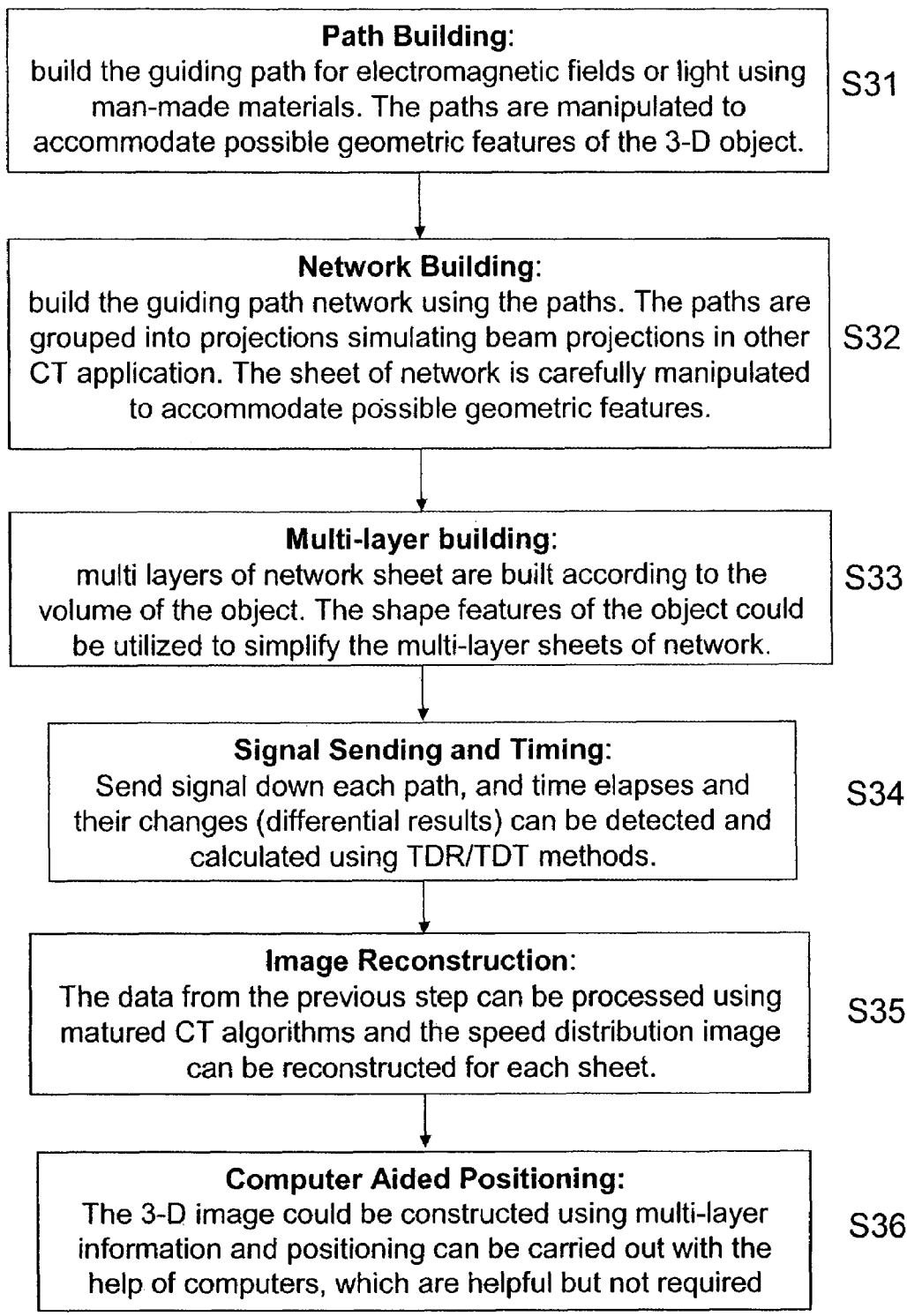
FIG. 3 notionally depicts the steps in a method for dealing with a three-dimensional ("3-D") media or body interface.

If the real-world problem is not a plane or a curved interface, a 3-D application may be necessary or desirable. FIG. 3 notionally depicts the following in steps S31, S32, S33, S34, S35, and S36.

Lets assume a situation where a 3-D body is composed of homogeneous media. Over time, the media will begin to become heterogeneous. This change may be detrimental to the desired properties of the body and we want to detect this process and evaluate the seriousness of the result. This would be a typical traditional open-beam CT application, if the 3-D body is actually a part of a human body, an industrial material under investigation, etc. In reality, however, field applications always require large-scale and relatively less expensive monitoring technique and traditional CT cannot handle this. On the other hand, the present disclosure regarding Guided TDR/TDT CT can be very useful.

We can still follow the steps in plane and curvy interface situation. The difference from them is that the guiding path network has to be 3-D instead of 2-D in order to monitor the whole body under investigation.

The difference between 3-D Guided TDR/TDT CT and traditional CT application in this application is that the guiding paths used to simulate the open beams can be flexible, and thus can be manipulated to accommodate the geometric features of the 3-D body under investigation.

For example, if the 3-D is symmetric in one direction and the guiding paths can be implemented according to this feature and thus lower the difficulty of the data processing and enhance the accuracy.

Guided TDR/TDT CT usually applies to relatively large-scale objects, and the resolution may not be a very critical issue. For example, if there is an area on the interface is questionable, there likely would be an opportunity to investigate. The geometry of the area under investigation may be more regular than traditional CT, such as round, elliptical, etc. The number of questionable areas may be relatively smaller than traditional CT application too. All of these considerations together dramatically decrease the requirement of resolution on Guided TDR/TDT CT. Accordingly, the number of projections or transmission guiding paths would increase. On the other hand, Guided TDR/TDT CT employs installed guiding paths to compose projections, thus the number of projections can be reduces compared to traditional CT due to physical limitations.

A method and system as in this disclosure with relatively lower resolution compared to that in traditional CT is not necessarily a drawback because the requirement on resolution is also lower. TDR/TDT results, on the other hand, can be understood in a different way besides the use of time integral. For example, reflection signal bumps in TDR can be used to back up the TDR CT analysis results. Thus this limitation may be compensated and decreased, and lifted.

Figure 5A:
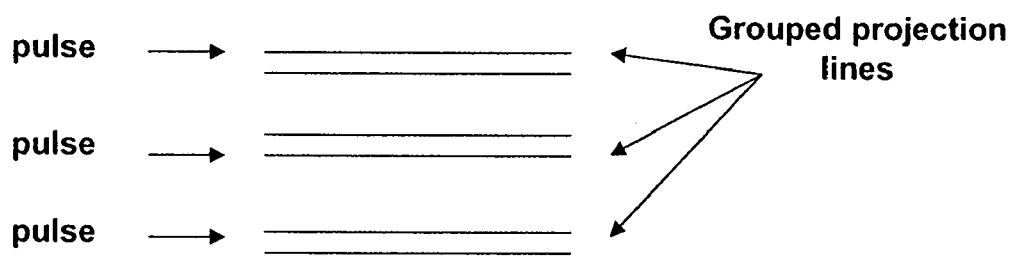
FIG. 5A illustrates three groups of projection lines each comprising multiple wires.
Figure 5B:
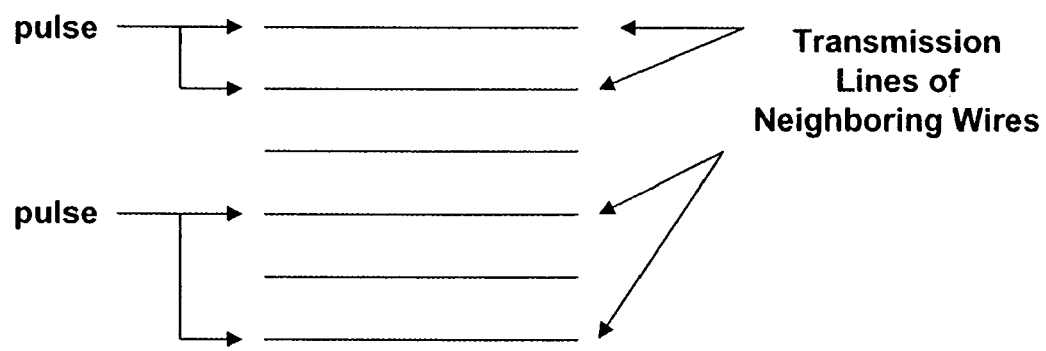
FIG. 5B illustrates neighboring wires grouped to form a transmission line model.

For all three situations discussed above, the projection lines are separated from other lines in the same projection group and in the other projection groups. There should not be direct electrical contact between each line unless the contact is used as an ending or starting of the transmission lines. FIGS. 5A and 5B illustrate examples of spacing and separation of projection lines.

If electromagnetic fields are employed and the electromagnetic guides have to be formed using multiple wires (or conductors), there are two ways to reach this goal: (1) Each single projection line can form a standby transmission line model by incorporating two or more wires (conductors) within the line. In this way, electromagnetic pulses used to detect defects can be sent down each single projection line. (2) If the spacing of the projection lines within each group is appropriate, the neighboring lines may comprise a transmission line model.

FIG. 5B shows two examples of transmission line compositions using two adjacent wires or first and third wires. As long as the spacing between two wires is appropriate according to requirements, the two wires can be first and forth, or fifth or other ones.

In alternative embodiments of this disclosure in which optical fibers are used, each fiber can form a guide by itself.

Specific Example

Monitoring of Surface Soil Moisture Level

The following example illustrates the idea and the entire process. The equipment and methods used in this example are depicted in FIGS. 7A-7G and are exemplary only. The actual applications of Guided TDR/TDT CT are not limited to specific equipment and methods discussed.

Figure 7A:
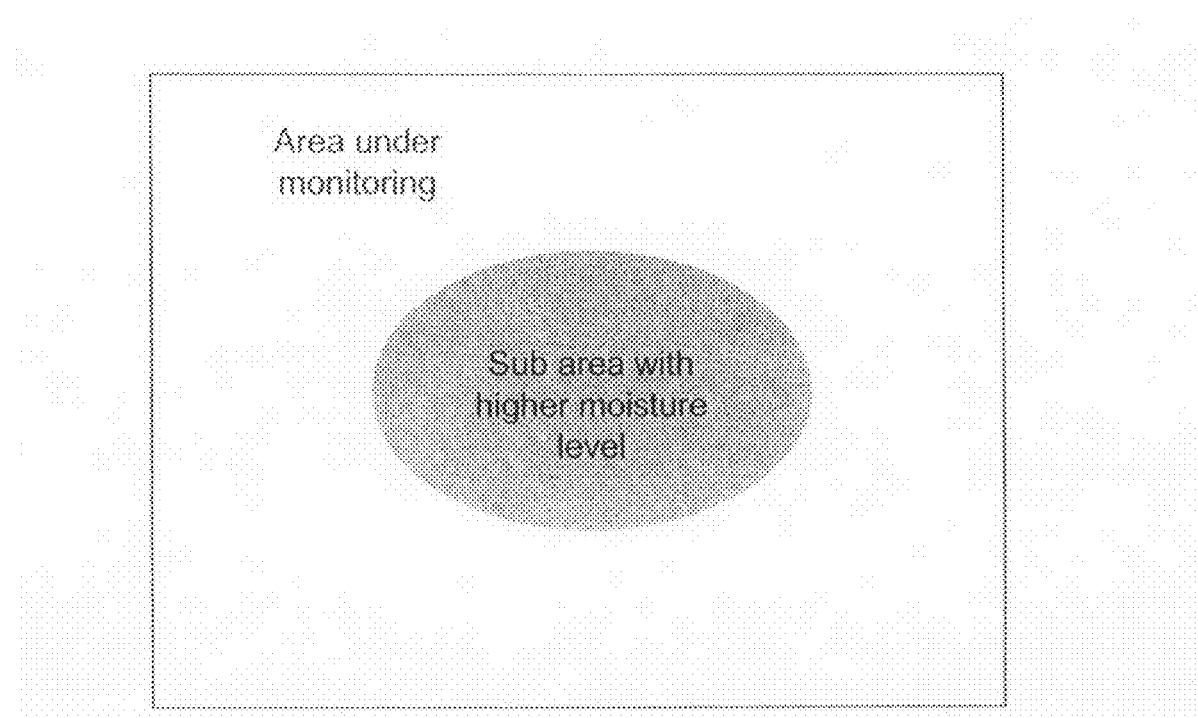
FIG. 7A illustrates a simplified plan view of an exemplary monitoring situation.

Assume that there is an area where the moisture level of the surface soil is to be monitored. Further assume that there is an elliptical sub area that changes moisture level as time passes. A process is needed to accurately monitor the area to detect a higher moisture content area, and locate this elliptical area when it occurs. FIG. 7A provides a plot illustrating the are under examination.

The gray area in FIG. 7A is the sub area with higher moisture level. We desire to detect and locate this sub area, and determine what its range is and when it occurs. We use TDR equipment (FIGS. 7D and 7E) and a TDR CT network sheet (FIG. 7G) to solve this problem. Specifically, an Agilent 54750A digitalizing oscilloscope (FIG. 7D) with an Agilent 54754A TDR module (FIG. 7E) are used.

The Agilent 54754A TDR module has a TDR and TDT port. In this application, we only use the TDR port. The TDR port in this module can send a 200 mV pulse down a transmission line and can also detect the reflected signal. The Agilent 54750A digitalizing oscilloscope can record the reflected signal sent and detected by the 54754A module and finish the analysis task.

Figure 7B:
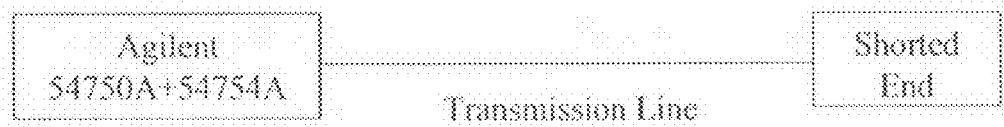
FIG. 7B depicts a notional system block diagram of a TDR CT system that may be used in conjunction with the exemplary monitoring situation of FIG. 7A.
Figure 7C:
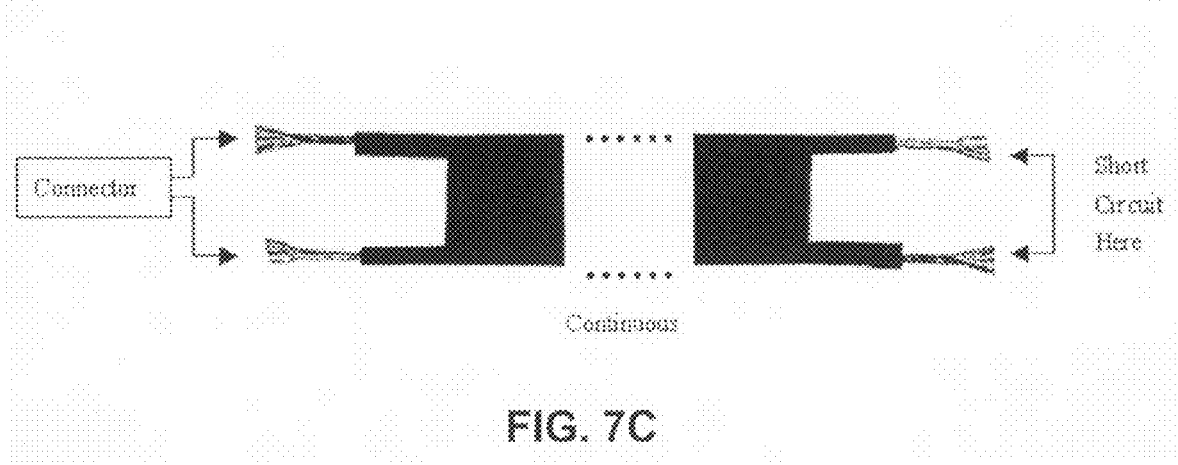
FIG. 7C provides an illustration of an exemplary flat ribbon transmission line that may be used in embodiments of the disclosure, including in the exemplary TDR CT system of FIG. 7B.
Figure 7E:
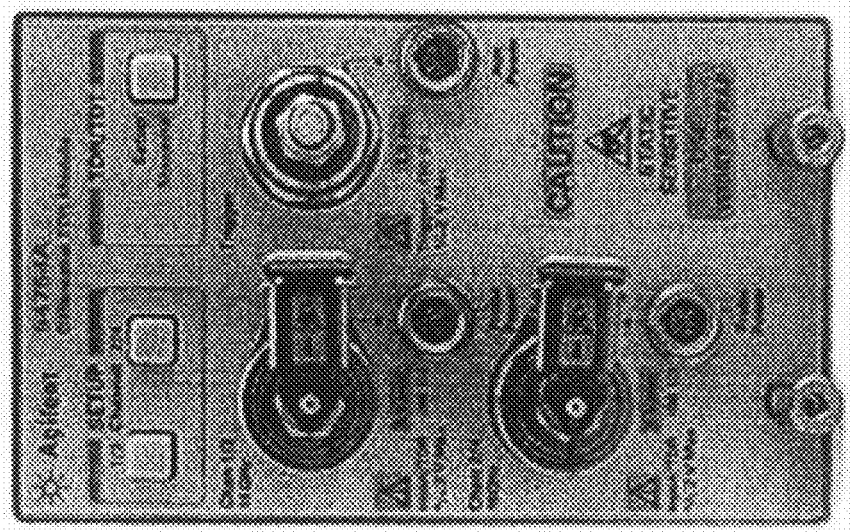
FIG. 7E provides a front panel view of the Agilent 54754A TDR module that may be used in the exemplary TDR CT system of FIG. 7B.
Figure 7D:
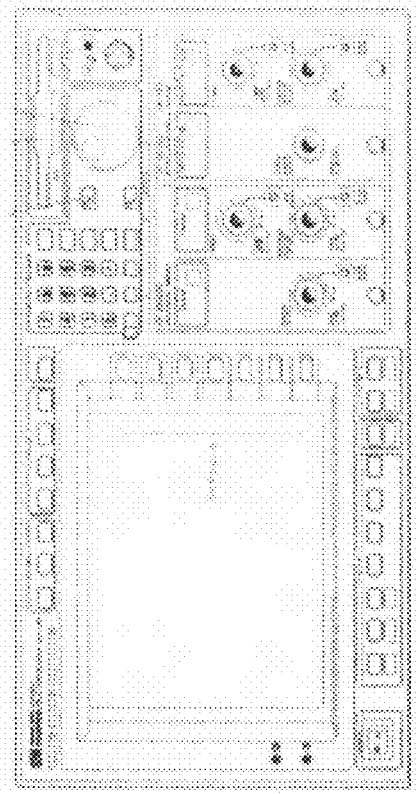
FIG. 7D provides a front panel view of the Agilent 54750A digital oscilloscope that may be used in the exemplary TDR CT system of FIG. 7B.
Figure 7F:
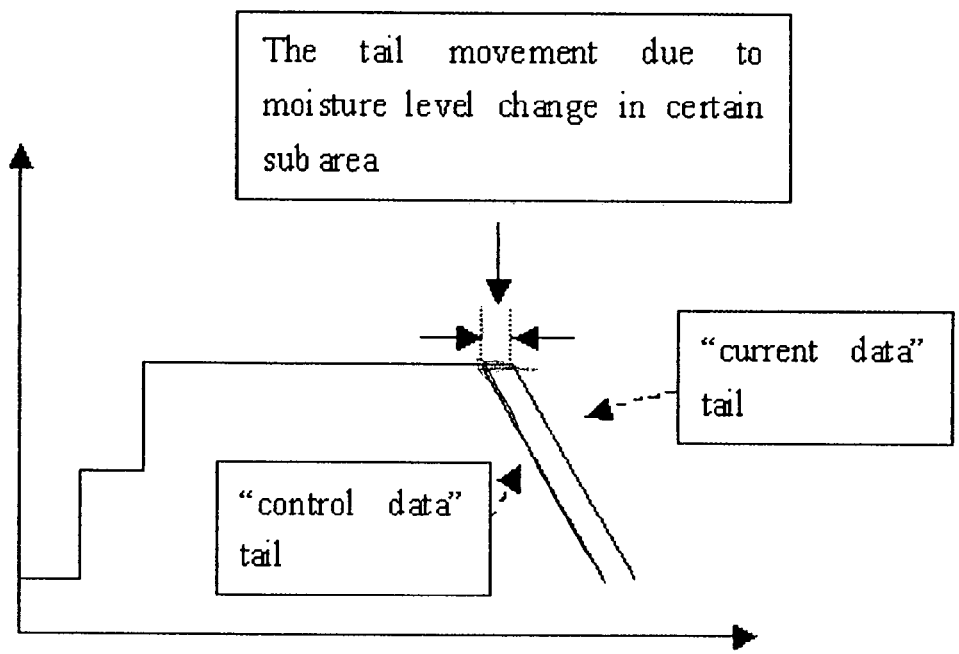
FIG. 7F illustrates a notional TDR plot showing the change in timing data of a reflected pulse over time as might be encountered in the exemplary monitoring situation of FIG. 7A.
Figure 7G:
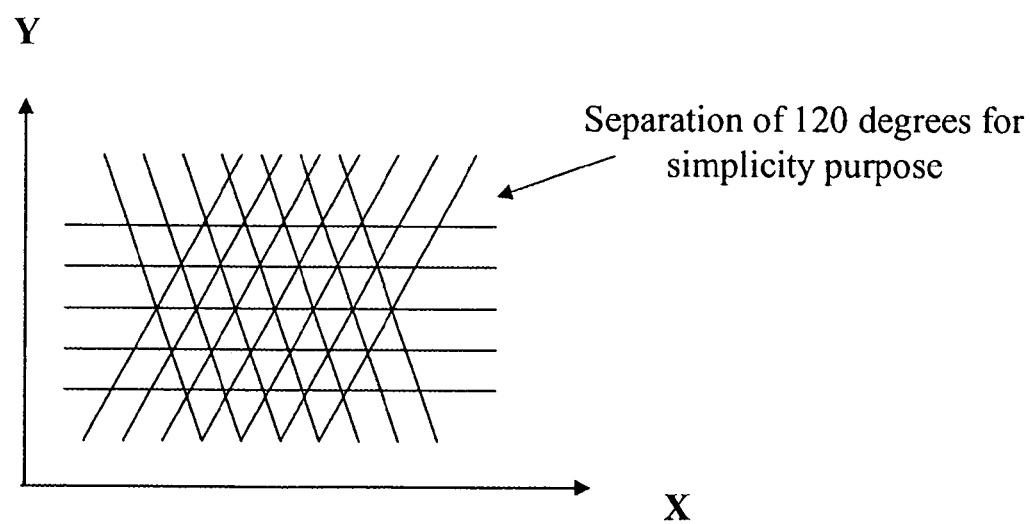
FIG. 7G illustrates an exemplary triangular network grid with 120° transmission line separation/offset that may be used in conjunction with the exemplary TDR CT system of FIG. 7B.

In this example, the TDR CT network sheet of FIG. 7G may be used. To make the solution simpler, we use a projection method composed of three groups of line integrals. These 3 groups are symmetrically 120 degrees offset from each other. Each line integral is actually a transmission line composed as shown in FIG. 7C.

Each individual transmission line (line integral) comprises a twin lead cable with a certain space between the two conductors. One end is shorted, and the other end is connected to the TDR module using a connector.

FIG. 7B illustrates the measurement setup on one single projection line. Each projection line would also be connected to a TDR signal generator/detector. The measurement setup on one single projection line is shown in the plot. The step pulse is sent by the Agilent 54750A (oscilloscope) and 54754A (TDR module) down the transmission line (twin lead cable). Then the original signal and reflected signal are recorded by the Agilent 54750A and 54754A.

The TDR CT network sheet in the area under monitoring is built using the previous methods of projection groups of transmission lines, and is set up in the area where the moisture level needs to be monitored. Because we want to monitor the moisture level in the topsoil, we can set up the network sheet in the way that it will follow the planar shape of the area right beneath the surface. Once the network sheet is setup, a group of control data of timing information is taken on each individual transmission line. The area may then be monitored over time by taking new data regularly or when needed. From this acquired time series of data, differential data results may be stored.

For each set of data collected, the differential results will be obtained by subtracting the control data from new data. This task will be carried out against each individual transmission line. The differential results then include the time integral information of the moisturized area along each transmission line (each line integral), assuming that timing information in non-moisturized area will not change with time elapse, and thus will be canceled during the differential process.

Image reconstruction is accomplished by using CT algorithms wherein the differential time integral results from each transmission lines are then fed into a CT algorithm software package or similar CT data processing algorithm and the EM speed distribution image will then be reconstructed allowing completion of detection and positioning.

The resolution of the reconstructed image is related to the number of projection groups, the spacing of transmission lines, and some other factors. Each transmission line in the network sheet will be connected to the oscilloscope and a TDR plot will be obtained by sending a step pulse down the line and recording the reflections. A typical TDR plot is shown in FIG. 6B wherein the signals recorded in the plot above show the beginning of step pulse, the connection cable, transmission line, and the tail. The transmission line runs through the area under monitoring and the signal length in the plot represents the total time elapse (time integral) for the Electromagnetic pulse to travel through.

Over time, for example, 6 months, if there is moisture level change in a certain sub area on the transmission line path as assumed, the signal length will then change and the tail will start to move in the signal record chart. This data can be recorded using TDR unit as "current data". FIG. 7F shows the control data and the "current data" on the same plot.

A differential tail movement result can then be obtained by subtraction of control from the current data. This differential result is also the time integral result of the moisturized area minus the same area before getting moisturized. This data is the one obtained on this particular transmission line and ready to be fed into CT data processing stage together with data from all other transmission lines.

As discussed above, the TDR CT network sheet is actually composed of groups of transmission lines. The control data and current data can be obtained from each individual transmission lines and thus the differential results can also be obtained on each individual transmission lines. All these differential results comprise a data package that will be fed into CT data processing software.

After all the differential data from each individual transmission line is obtained, the package of data is fed to a CT data processing unit, which is usually a software package built using matured CT technology and algorithms. The distribution of electromagnetic field speed in the area under monitoring can be calculated and distribution image can be reconstructed. Thus the moisturized area can be indicated on the reconstructed image plot.

Software Algorithm

TABLE I below provides an exemplary illustration of conventional MATLAB code modified to change the example from a checker board pattern to an elliptical shape which appears to be more practical for simulating a moisturized area. The software algorithm/code may be used to finish the projection an reconstruction process.

The following code in TABLE I may be executed by a MATLAB program, after which the reconstruction results will be displayed. Although the following algorithm was developed for x-ray tomography, it also has application in this disclosure.

TABLE I

Exemplary software algorithm

```
% This is MATLAB code which does the CT reconstruction for
% parallel beam x-ray tomography. The code has been written to verify
% the correctness of the FORTRAN algorithm.
% The program will give an image pertaining to the projection
% data by making gray scaled image of the final data.
% It takes about 15 minutes on a Sun Sparc 10 for an image of 64×64
pixels.
clear; tau=1.0; rays=16; angles=5; flops(0);
% In this program the variable, tau is set to unity, but is defined
% in more general terms on pgs. 71-72 (FIG. 3.14) "Kak and Slaney".
mp=rays/2.0;
x_min=1
x_max=rays;
x_cen=((x_max)/2.0)
y_min=1
y_max=rays;
y_cen=((ymax)/2.0)
x_max2 = 64;
y_max2 = 64;
x_cen2 = x_max2/2;
y_cen2 = y_max2/2;
aa2=((x_max)/4.0)∧2;
bb2=((x_max)/6.0)∧2;
pi = acos(-1.0)
disp('Calculations in progress. . .');
%initialize the object, the original pattern, to zeros
disp('initlalizing the object');
```

TABLE I-continued

Exemplary software algorithm

```
for i = 1:x_max,
    for j = 1:y_max,
        object(i,j) = 0;
    end;
end;
% initalize the projection matrix to zero:
% simulated parallel xray projections [eqn(3) pg. 50]
disp('initlalizing the projection matrix');
    for i = 1:angles,
        for j = 1:rays,
            A(i,j) = 0;
        end;
    end;
nf1=flops;
% This routine generates data of the original object: (x_max, y_max),
% The pattern is supposed to look like a checker board.
% Make a checker board pattern, see FIG. 4.6 pg. 36 of this report.
    blank =0;
        for i = 1:1:x_max,
            for j = 1:1:y_max,
                if ((i-x_cen)∧2)/aa2+((j-y_cen)∧2)/bb2 <= 1 object(i,j)=0;
                else
                    object(i,j) = 255;
                end;
            end;
        end;
nf2=flops;
% Chris Henze's ramp function: (Biology)
disp('generating the ramp');
a1 = linspace(0,32,32);    % create linear ramp, pg 168 MATLAB
hf = [a1 fliplr(a1(1:32))];  % flip left-to-right, pg 77 MATLAB
H = hf .* hamming(64)';   % Hamming funct, pg 168 MATLAB
nf3=flops;
disp('Using Hamming Window N =64');
% projecting the data points. The projections are
% 64 angles X 16 rays per angle.
disp('Projecting the object');
% The factor=1.15 in the denominator requires some explanation.
% Ideally this should be just 1/sqrt(2). This factor,
% 1/sqrt(2), is the worst case at a rotation of 45 degrees where
% the object always fits inside a square whose edge dimension is
% the largest dimension of the original object. Pragmatically,
% this factor 1.15 has been put in the denominator so that rays
% always fit within the object. When the rays fall outside of the
% object, although the result should be near zero, a numerical
% error results. If 1.15 is changed to 1.0 this program will not
% run. An alternate technique may work if the uneven object fits
% into a circle instead of a square, where the largest object
% dimension becomes the diameter of the circle.
tw=1/(1.15*sqrt(2));
% Calculate the forward projections: Kak & Slaney pgs. 49-56
% This is where the CM5 does not parallelize well, but we can
% use the Paragon to parallelize this section by assigning
% rows(angles) to each cpu(node).
for x=x_min:x_max,
    for y=y_min:y_max,
        sum=0.0;
        for i=1:angles,
            theta = (i-1)*pi/angles;
r = cos(theta)*((x-x_cen)/(x_cen))+sin(theta)*((y-y_cen)/(y_cen));
            mb = (r*mp*tw)+mp;
            lb = floor(mb);hb=ceil(mb);frac=mb-lb;
            A(i,lb) = A(i,lb) + ((1-frac)*object(x,y));
            A(i,hb) = A(i,hb) + (frac*object(x,y));
        end;
    end;
end;
disp('forward projections completed');
nf4=flops;
% Calculate the 1D FFT, Step 1, pg 15 Report, also eqn(2.4)
for i=1:angles,
    for j=1:rays,
        p1(j)=A(i,j);
    end;
% pad with zeros to the right of the matrix p1
    p = [p1 zeros(1,48)]; % Extend p1(16) to 64 by padding with zeros
    a2 = fft(p);
```

TABLE I-continued

Exemplary software algorithm

```
% The next three lines could be eliminated but they
% were included here to view intermediate values
% for j=1:length(a2),
% A2(i,j)=a2(j);
% end;
% Recall, H, Hamming operation, see the inside integral of eqn(33) pg 64
% of Kak & Slaney. Also see this same operation on the bottom line of
% eqn(69) on pg 75, H = [FFT h (n t) with ZP]×smoothing-window}.
    dtime=fft(p) .* H;
% Again the next three lines could be eliminated but they
% were included here to view intermediate values
% a3 = dtime;
% for j=1:length(a3),
% A3(i,j)=a3(j);
% end;
% The left operation of eqn(69)
    d = ifft(dtime);
    for j=1:length(d),
        c(i,j)=d(j);
    end;
% This is the end of the loop on angles
end;
disp('Filtered Projections Completed');
nf5 = flops;
disp('backprojecting. . .');
% This is the final step of backprojecting the results into array f(x,y).
% This is the summation of step 4 eqn(2.21) on pg 15 in this report,
% also eqn(45) on pg 67 of Kak & Slaney.
% This operation is similar to the forward projection
% except now we have to sum (this sum can be divided over cpu's)
% instead of the arbitrary "random" accumulation of values of the forward
projection.
% Comment: This part is important for both the CM5 & the Paragon:
each
% of these machines parallelize this sum differently but this is the most
% important part of the total time on either machine and represent the
% section that benefits the most from the parallelization on the CM5 or
% the Paragon.
    for x=x_min:x_max2,
        for y=y_min:y_max2,
            sum=0.0;
            for i=1:angles,
                theta = (i-1)*pi/angles;
r = cos(theta)*((x-x_cen2)/(x_cen2))+sin(theta)*((y-y_cen2)/(y_cen2));
                mb = (r*mp*tw)+mp;
                lb = floor(mb);hb=ceil(mb);frac=mb-lb;
                sum = sum + real(c(i,lb))*(1-frac) + frac*real(c(i,hb));
            end,
            f(x,y)=sum;
        end;
    end;
disp('backward projection completed');
disp('store reconstructed image to f.dat');
save f.dat f/ascii
disp('DONE')
imshow(f) % Display the reduced image.
%fid = fopen('mag.gray','wb');
%fwrite(fid,fgray,'real');
%nf6=flops;
%save ct26_0117.mat;
%quit;
```

Simulation Results

An example of image reconstruction using computerized tomography technique to process the TDR/TDT differential results data to reconstruct the image of a moisturized land area using the MATLAB code above will now be discussed.

The following discussion is provided in two parts, where the first one idealizes the unknown moisturized area and illustrates how the image is reconstructed using imaginary data. The second part explains how to incorporate real experimental data into a software program and reconstruct the image of the real moisturized area.

This example is for illustration purposes only to demonstrate that the novel concept of this disclosure is workable, and the following process may not necessarily be optimized.

Figure 8A:
FIG. 8A illustrates an exemplary digitized "elliptical" area, wherein a moisturized area is depicted by the black area.

1. Illustration of a Hypothetical Case:

Assume an elliptical moisturized area in the center of a square digitalized for the purpose of facilitating the input of information to a computer program. The digitalized ellipse is shown in FIG. 8A. The issue is how to detect it and reconstruct the image.

This example assumes that the moisturized area (the dark elliptical digitalized area in the center) is filled with color or grayscale number 255 (BLACK) while the non-moisturized area is filled with color number 0 (WHITE). We will see in the discussion below that the color number 255 represents the time delay due to moisture, and color number 0 represents no time delay, i.e., no moisture.

As mentioned above, a computer software program may be used to recreate an image representing the moisturized area. When the process starts, the program will first apply projection on the whole square area without "knowing" there is a dark elliptical area in the center. Then CT analysis method will be employed to reconstruct the image of the square area based on the projection data. When the reconstruction process is finished, the image of the square area is shown. and now the reconstructed image of the elliptical area is also visible and will be compared to the original one.

Figure 9:
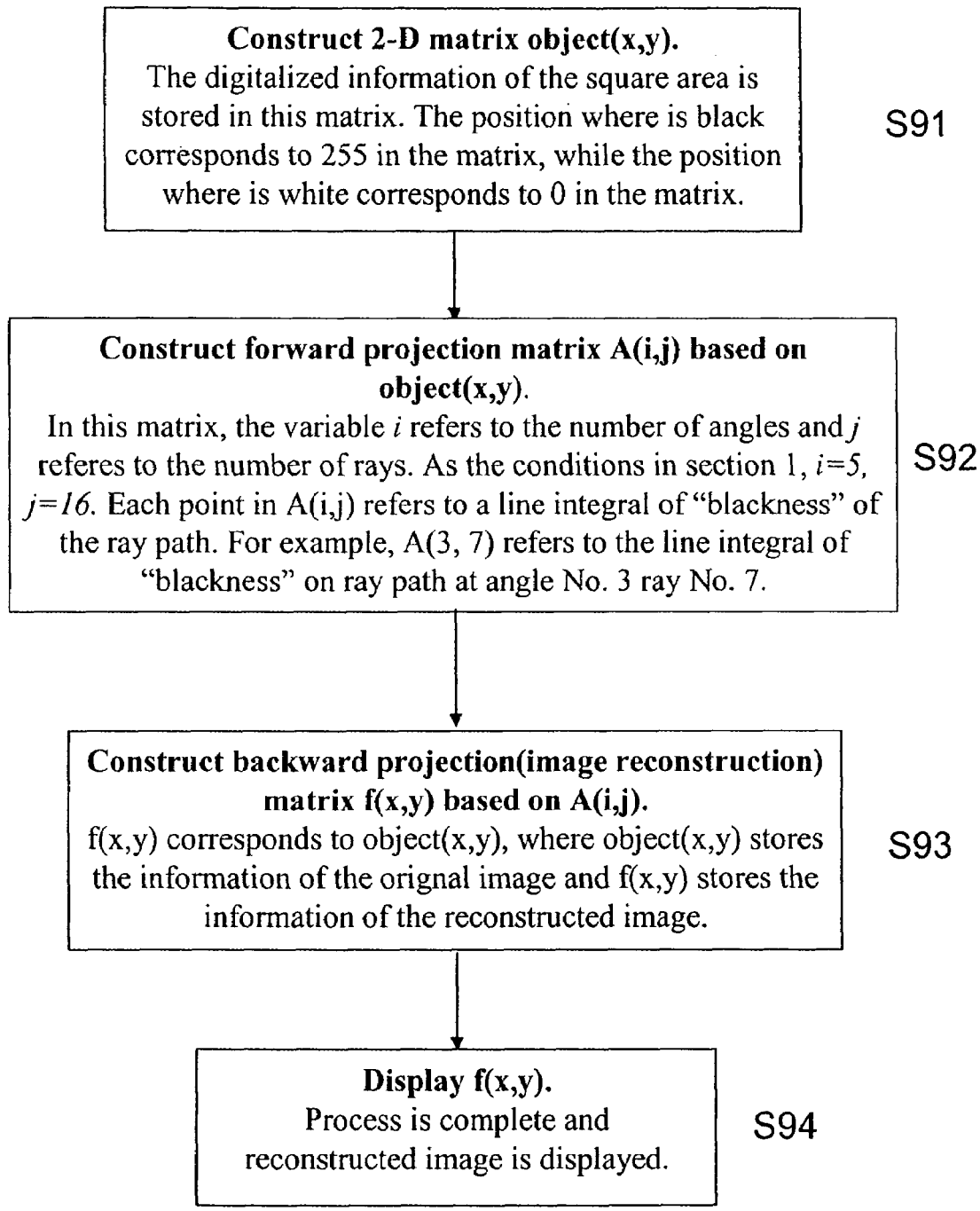
FIG. 9 illustrates a flow chart of exemplary steps to reconstruct a TDR/TDT CT image.

FIG. 9 provides a flowchart illustrating various aspects of the algorithm in TABLE I.

Figure 8B:
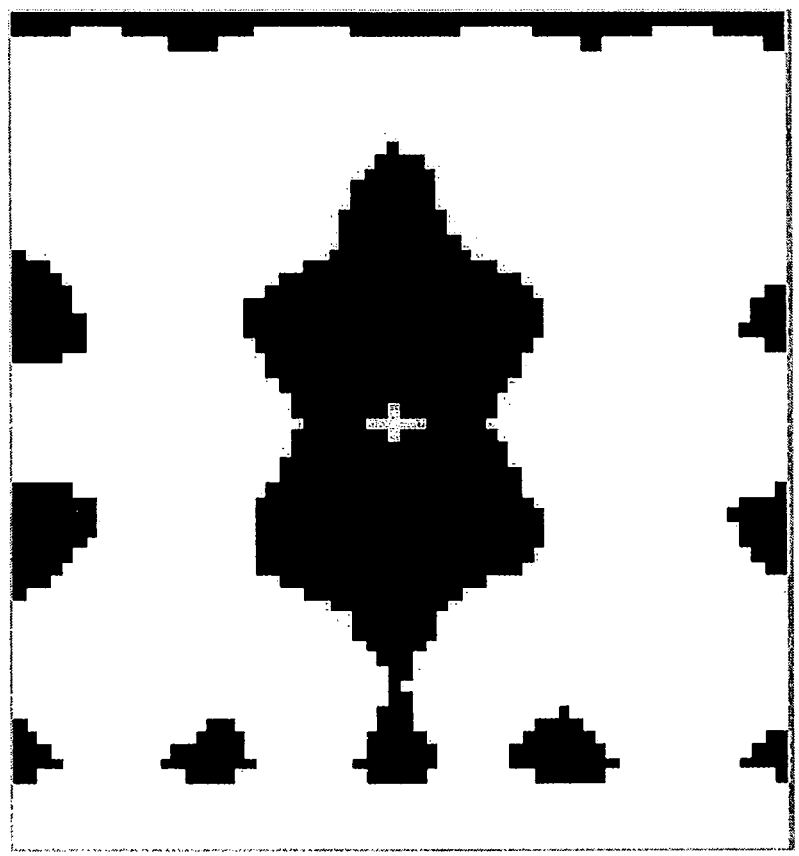
FIG. 8B illustrates an exemplary image reconstruction.

FIG. 8B illustrates the results of simulation, which looks very similar to the original elliptical shape of the moisturized area. Of course, other software algorithms could be adapted for the purposes described in this disclosure.

Conditions of the Program Simulation:

The simulation uses 16 rays on each angle of projection (corresponding to 16 transmission lines/wave guides using man made material/optical guides etc. in the TDR/TDT CT method), 5 projection angles (corresponding to 5 projection angles in TDR/TDT CT).

The result is obviously very satisfactory in practice, considering that the algorithm has not necessarily been optimized according to practical aspects. In addition, once the suspect area is found on the plot, further investigation can made. For the purpose of monitoring, the results appear to be satisfactory, as the quality of the reconstructed image in this example is not extremely critical, as is the case in medical imaging applications using x-ray CT, for example.

2. Illustration of a Real Case—how to Use the Code to Reconstruct a Real TDR/TDT CT Image:

The structure of the code in section 1 above is illustrated in FIG. 9.

If we assume that we use similar conditions in the square area where we monitor moisture levels in the real case. We then have the real process for reconstructing the real moisture image 1. We bury 16 transmission lines (could be wave guides/ optical guides, etc, depending on application methods) in parallel in each angle with totally 5 angles in the square area to construct the grid mentioned before.

2. We first use EM pulses to take a control data matrix $A1(i,j)$ in which each point refers to the TDR/TDT data collected on the single transmission line at a particular angle. For example, again, $A1(3,7)$ refers to the TDR/TDT data on line No. 7 at angle No. 3. Further assume that we monitor the moisture level change over 6 months. Then 6 months later, a second group of data matrix $A2(i,j)$ is taken. $A2(i,j)$ has the same format and order as $A1(i,j)$ except $A2(i,j)$ is the data 6 months later. Then a differential result $A(i,j)=A2(i,j)-A1(i,j)$ is calculated. Each point in A(i,j) now contains a line integral of time delay because of moisture distribution on the path.

3. Feed A(i,j) to the program (the program has to be modified to get experimental data matrix A(i,j), rather than constructed data matrix as in section 1. It is a very simple modification) and reconstruct the image matrix of f(x,y) which contains the moisture information of each point in the square area.

4. Display f(x,y) as an image. The moisturized area is now visible.

Figure 10:
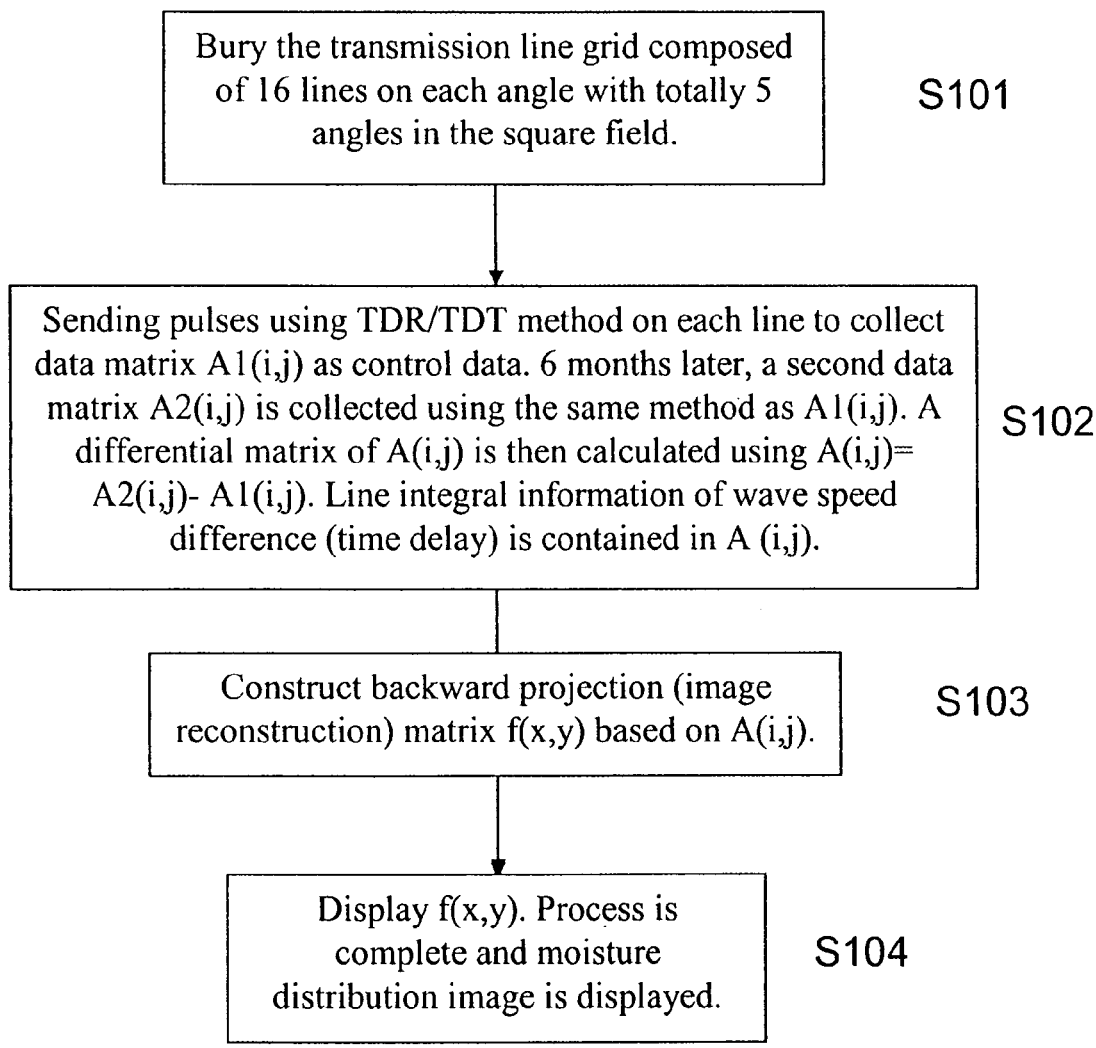
FIG. 10 illustrates a flow chart of alternative exemplary steps to reconstruct a TDR/TDT CT image.

So, now the structure of the program used for the real case moisture image reconstruction is slightly different from the one used in section 1 for imaginary image reconstruction. The modified flowchart for the real case above is depicted in FIG. 10.

Lets assume that in the real case, the moisturized area is actually an elliptical shape in the center of the square area just like in section 1 and the moisture level in this sub-area is identical. Then the reconstructed image f(x,y) will now be the same shape as f(x,y) in section 1.

Again, this example is to demonstrate novel aspects of the process and the idea, and may be further optimized to the degree necessary, depending on the particular details of the application.

The above description and examples are not meant to be limiting in any respect, but are merely intended to provide a description of exemplary embodiments such that a person with skill in the art could derive alternative embodiments from the novel concept described herein.

What is claimed as new and desired to be protected by Letters Patent of the United States is:

1. A method of detecting a defect or discontinuity in media or at an interface between the media, the method comprising:
   establishing an electromagnetic energy guide path through the media;
   coupling electromagnetic energy into the guide path;
   detecting a reflected portion of the electromagnetic energy out of the guide path; and
   analyzing the detected portion so as to determine a position of the defect or discontinuity,
   wherein said establishing the electromagnetic energy guide path comprises establishing a grid through the media,
   wherein the grid comprises a plurality of transmission paths operatively decoupled from each other along their entire length.

2. The method of claim 1, further comprising:
   establishing a baseline condition of the media at a first time value;
   determining a condition of the media after the first time value; and
   comparing the condition of the media to the baseline condition.

3. The method of claim 1, wherein the grid comprises a two-dimensional grid.

4. The method of claim 1, wherein the grid comprises a three-dimensional grid.

5. The method of claim 1, wherein said coupling electromagnetic energy comprises coupling a pulsed signal into the guide path and detecting timing of a movement of a pulse edge.

6. The method of claim 1, wherein said analyzing the detected portion comprises using a TDR/TDT technique.

7. The method of claim 1, further comprising reconstructing an image using a computerized tomography technique.

8. The method of claim 1, wherein said coupling electromagnetic energy comprises coupling RF energy into the guide path.

9. The method of claim 1, wherein said coupling electromagnetic energy comprises coupling light energy into the guide path.

10. A system for detecting a defect or discontinuity in media or at an interface of the media, the system comprising:
    a signal generator configured to generate an electromagnetic energy signal;
    a plurality of transmission paths coupled to the signal generator, the plurality of transmission paths configured to guide the electromagnetic energy signal and arranged in a grid through the media, wherein the plurality of transmission paths are operatively decoupled from each other along their entire length;
    a detection circuit for detecting a transmitted and a reflected portion of the electromagnetic energy signal provided by the signal generator passing through the plurality of transmission paths; and
    a circuit for analyzing the reflected portion and identifying a location of a discontinuity or defect in the media.

11. The system of claim 10, wherein said transmission path comprises a transmission line.

12. The system of claim 10, wherein said transmission path comprises an optical fiber.

13. The system of claim 10, wherein the grid comprises a two-dimensional grid.

14. The system of claim 10, wherein the grid comprises a three-dimensional grid.

15. The system of claim 10, wherein said electromagnetic energy signal provided by the signal generator comprises a pulsed signal.

16. The system of claim 10, wherein said circuit comprises a TDR/TDT analyzer.

17. The system of claim 10, further comprising a computer circuit for reconstructing an image.

18. The system of claim 17, wherein said computer circuit for reconstructing an image uses a computerized tomography technique.

19. The system of claim 10, wherein said signal generator generates RF energy.

20. The system of claim 10, wherein said signal generator generates light energy.

21. The system of claim 10, further comprising a computer circuit for:
    establishing a baseline condition of the media at a first time value;
    determining a condition of the media after the first time value; and
    comparing the condition of the media to the baseline condition.

22. The system of claim 11, wherein the transmission line is open circuited.

23. The system of claim 11, wherein the transmission line is short circuited at an end distal from said signal generator.

* * * * *